United States Patent

Fero et al.

[11] Patent Number: 5,781,602
[45] Date of Patent: Jul. 14, 1998

[54] PGNAA SYSTEM FOR NON-INVASIVELY INSPECTING RPV WELD METAL IN SITU, TO DETERMINE THE PRESENCE AND AMOUNT OF TRACE EMBRITTLEMENT-ENHANCING ELEMENT

[75] Inventors: Arnold H. Fero, New Kensington; Stanwood L. Anderson, Pittsburgh; Thomas V. Congedo, Pittsburgh; Abdul R. Dulloo, Pittsburgh; Francis H. Ruddy, Monroeville, all of Pa.

[73] Assignee: Westinghouse Electric Corporation, Pittsburgh, Pa.

[21] Appl. No.: 649,370

[22] Filed: May 17, 1996

[51] Int. Cl.$^6$ ................................................. G21C 17/003
[52] U.S. Cl. ........................................... 376/159; 376/249
[58] Field of Search ................................. 376/157, 159, 376/160, 161, 162, 245, 249

[56] References Cited

U.S. PATENT DOCUMENTS

| | | | |
|---|---|---|---|
| Re. 27,579 | 2/1973 | Youmans | 376/159 |
| 2,395,322 | 2/1946 | Evans | 97/47 |
| 2,557,158 | 6/1951 | Teichmann | 250/83.6 |
| 2,562,914 | 8/1951 | Herzog | 250/83.6 |
| 2,781,453 | 2/1957 | Belcher et al. | 250/83.6 |
| 2,800,857 | 7/1957 | Bennett | 97/46.39 |
| 3,008,046 | 11/1961 | Carpenter | 250/71.5 |
| 3,124,684 | 3/1964 | Eberline | 250/71.5 |
| 3,256,438 | 6/1966 | Armistead | 376/159 |
| 3,341,706 | 9/1967 | Swift et al. | 250/83.3 |
| 3,354,310 | 11/1967 | Swift | 250/83.3 |
| 3,433,310 | 3/1969 | Harper | 172/471 |
| 3,444,721 | 5/1969 | Hearn et al. | 73/23 |
| 3,463,922 | 8/1969 | Senftle et al. | 376/159 |
| 3,612,874 | 10/1971 | Porter | 376/159 |
| 3,715,758 | 2/1973 | Sender | 343/112 R |
| 3,723,727 | 3/1973 | Wogman et al. | 250/83.3 |
| 3,781,556 | 12/1973 | Taylor et al. | 250/302 |
| 3,801,816 | 4/1974 | Arnold | 250/270 |
| 3,812,364 | 5/1974 | Higatsberger et al. | 376/159 |
| 3,825,751 | 7/1974 | Johnson, Jr. et al. | 250/253 |
| 3,832,545 | 8/1974 | Bartko | 250/312 |
| 3,889,112 | 6/1975 | Holmes et al. | 250/265 |
| 3,918,056 | 11/1975 | Merrick | 343/6.5 LC |
| 3,938,146 | 2/1976 | Dano | 343/6.5 LC |
| 4,056,969 | 11/1977 | Barringer | 73/28 |
| 4,232,220 | 11/1980 | Hertzog | 250/270 |
| 4,232,317 | 11/1980 | Freeny, Jr. | 343/112 |
| 4,248,310 | 2/1981 | McWilliams | 172/661 |
| 4,278,885 | 7/1981 | von Alfthan et al. | 250/370 |
| 4,302,285 | 11/1981 | Pronman et al. | 376/159 |
| 4,314,155 | 2/1982 | Sowerby | 250/253 |
| 4,317,033 | 2/1982 | Paneka et al. | 250/253 |
| 4,350,887 | 9/1982 | Barnard et al. | 250/265 |
| 4,421,981 | 12/1983 | Hough | 250/253 |
| 4,464,330 | 8/1984 | Speir et al. | 376/159 |
| 4,483,817 | 11/1984 | Evans et al. | 376/159 |

(List continued on next page.)

FOREIGN PATENT DOCUMENTS

| | | |
|---|---|---|
| 0 081 075 | 6/1983 | European Pat. Off. |
| 1236831B | 3/1967 | Germany. |
| 973322A | 10/1964 | United Kingdom. |
| 2148583A | 3/1985 | United Kingdom. |

OTHER PUBLICATIONS

Philips Technische Rundschak, vol. 34, No. 11/12, 1975, pp. 334–342.

Wolfgang E. Ernst et al., "Determination of Copper in A.533b Steel for the Assessment of Radiation Embrittlement Using Laser–Induced Breakdown Spectroscopy", Applied Spectroscopy, vol. 50, No. 3, 1996, pp. 306–309.

Clem, W.E., "Mobile Surface Contamination Monitor for Large Area Radiological Surveillance", Rockwell Hanford Operations, Richland, WA, pp. 1–4.

(List continued on next page.)

Primary Examiner—Daniel D. Wasil

[57] ABSTRACT

Prompt Gamma Neuteon Activation Analysis (PGNAA) is employed to determined in situ the content of nickel, copper, or other embrittlement-enhancing elements within the weld metal joints of nuclear reactor pressure vessels.

26 Claims, 1 Drawing Sheet

U.S. PATENT DOCUMENTS

| | | | |
|---|---|---|---|
| 4,581,531 | 4/1986 | Dion | 250/253 |
| 4,622,200 | 11/1986 | Gold et al. | 376/159 |
| 4,645,926 | 2/1987 | Randall | 250/270 |
| 4,728,482 | 3/1988 | Boyle et al. | 376/249 |
| 4,754,136 | 6/1988 | Blakely | 250/301 |
| 4,851,687 | 7/1989 | Ettinger et al. | 376/159 |
| 5,025,150 | 6/1991 | Oldham et al. | 250/253 |
| 5,038,042 | 8/1991 | Hansen et al. | 250/368 |
| 5,068,532 | 11/1991 | Wormald | 250/270 |
| 5,133,901 | 7/1992 | Peterson | 252/626 |
| 5,162,095 | 11/1992 | Alegre et al. | 376/159 |
| 5,539,788 | 7/1996 | Ruddy et al. | 376/159 |

OTHER PUBLICATIONS

Evans, L. et al., "Inter–Pulse High–Resolution Gamma–Ray Spectra Using a 14 MeV Pulsed Neutron Generator", *Nuclear Instruments and Methods in Physics Research* 1984, 219, 233–242.

Evans, L. et al., "In Situ Elemental Analysis Using Neutron–Capture Gamma–ray Spectroscopy", *Nuclear Instruments and Methods*, North–Holland, 1982, 353–357.

Evans, L. et al., "Determination of Elemental Composition in Geochemical Exploration Using a 14–MeV Neutron Generator", *IEEE Transactions on Nuclear Science, I. Experimental Aspects*, Apr. 1981, vol. NS–28 No. 2, 1626–1628.

Herzenberg, C., "Use of Small Accelerators in Coal Analysis and Coal Slurry Flow Measurements", *IEEE Transactions on Nuclear Science* Feb. 1979, vol. NS–26, No. 1, Part 2 of 2 Parts, 1568–1573.

Jensen, D.H., et al., "Status of a Pulsed–Neutron Logging Probe Using a High–Purity Germanium Detector", *IEEE Transactions on Nuclear Science* Apr. 1983, vol. NS–30, No. 2, 1657–1663.

Lapides, J., "Determination of Elemental Composition in Geochemical Exploration Using a 14–MeV Neutron Generators", *IEEE Transactions on Nuclear Science* Apr. 1981, vol. NS–28, No. 2, 1629–1631.

McKlveen, J., "A Compilation of Fast Neutron Interactions, Cross Sections, Gamma Spectra and Gamma Decay Energies", *IEEE Transactions on Nuclear Science* Apr. 1981, vol. NS–28, No. 2, 1632–1634.

Meyer, H.R. et al., "Field Instruments Developed for Radiation Measurements on the UMTRA Project", *Proceedings, Waste Management*, Mar. 1987, U. of Arizona.

Persignault, D. et al., "A Prompt Gamma–Ray Coal Analysis System", *Proceedings of the American Nuclear Society National Topical Meeting*, Apr. 19–21, 1971, Augusta, Georgia, pp. IV–40–IV–46.

Sowerby, B.D., "On–Line and Bulk Analysis of Coal", *J. of Radioanalytical and Nuclear Chemistry* Feb. 8, 1988, vol. 123, 61–75.

Worth, G.M. et al., "Use of Commercial ranging System in Field Surveys of Radioactively Contaminated Sites", *1984 IEEE Nuclear Science Symposium, Oct. 31–Nov. 2, 1984*.

"NRC Clears Palisade's Vessel For Operation Through 1999," *Apr. 1995 McGraw–Hill Inc. Nucleonics Week* Apr. 20, 1995, vol. 36(16), p. 6.

"RPV Welds May Become Brittle Faster," *Jun. 1995 American Nuclear Society Nuclear News* Jun. 17, 1995, p. 18.

"Duquesne Plans Neuttron Flux Reduction," *Jul. 1995 American Nuclear Society Nuclear News* Jul. 17, 1995, p. 20.

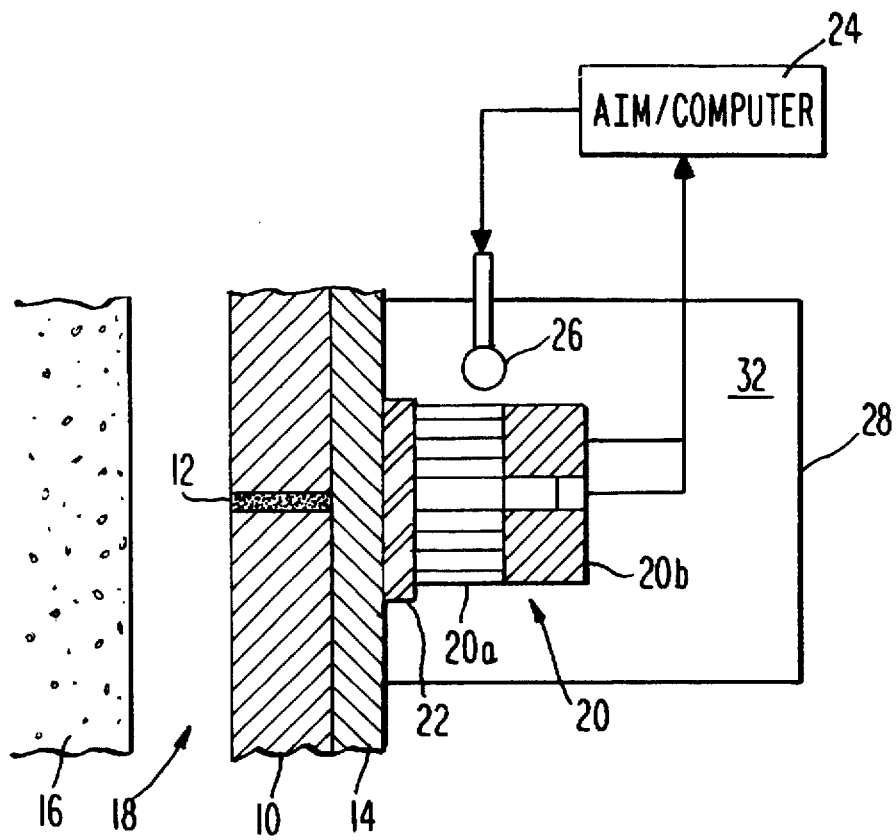
_Fig. 1_
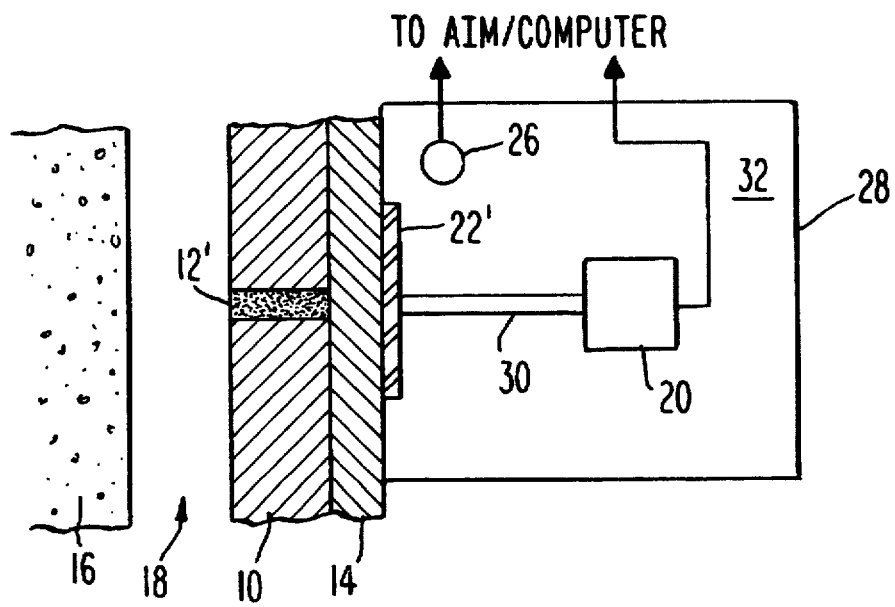
_Fig. 2_

PGNAA SYSTEM FOR NON-INVASIVELY INSPECTING RPV WELD METAL IN SITU, TO DETERMINE THE PRESENCE AND AMOUNT OF TRACE EMBRITTLEMENT-ENHANCING ELEMENT

BACKGROUND OF THE INVENTION

The present invention relates generally to methods and apparatus for inspecting pressurized water nuclear reactor pressure vessels (RPVs). The invention more particularly relates to a non-destructive method and system for interrogating, in situ, using Prompt Gamma Neutron Activation Analysis (PGNAA), the metal weld joints of an RPV to determine the content of nickel, copper or other elements that can cause a weld to become brittle.

The ability of the large steel pressure vessel of a nuclear reactor, which contains the reactor core and its primary coolant, to resist fracture is an important factor in ensuring safety in the nuclear industry. The beltline region of the RPV, generally corresponding to the region alongside the nuclear core, is the most critical region of the vessel because it is subjected to significant bombardment by fast, energetic neutrons. Fast neutron irradiation of low alloy ferritic steels causes such materials to show an increase in hardness and tensile properties and a decrease in ductility and toughness under certain conditions of irradiation. Therefore, such ferritic materials can cause the RPV to become brittle in the weld regions in which they reside.

A method for performing analyses to guard against fast fracture in reactor pressure vessels has been presented in *Protection Against Nonductile Failure*, Appendix G to Section III of the ASME Boiler and Pressure Vessel Code. This method uses fracture mechanics concepts and is based on the reference nil-ductility temperature ($RT_{NDT}$). The $RT_{NDT}$ of a given material is used to index that material to a reference stress intensity factor curve ($K_{IR}$ curve) that appears in Appendix G to the ASME Code. The $K_{IR}$ curve is a lower bound of dynamic, crack arrest, and static fracture toughness results obtained from several heats of pressure vessel steel. When a given material is indexed to the $K_{IR}$ curve, allowable stress intensity factors can be obtained for this material as a function of temperature. Allowable operating limits can then be determined using these allowable stress intensity factors.

The $RT_{NDT}$, and in turn the operating limits of nuclear power plants, can be adjusted to account for the effects of radiation on the reactor vessel material properties. The radiation embrittlement changes in a given RPV steel can be monitored by a reactor surveillance program, in which a surveillance capsule is periodically removed from the operating nuclear reactor and the encapsulated specimens tested. The increase in the average Charpy V-notch 30 ft-lb temperature ($\Delta RT_{NDT}$) due to irradiation is added to the initial $RT_{NDT}$ to adjust the $RT_{NDT}$ for radiation embrittlement. This adjusted reference temperature ($ART=IRT_{NDT}+\Delta RT_{NDT}+$ Margin) is used to index the material to the $K_{IR}$ curve and, in turn, to set operating limits for the nuclear power plant which take into account the effects of irradiation on the reactor vessel materials.

Estimates of $\Delta RT_{NDT}$ due to irradiation are based on the fluence of fast neutrons (defined as the number per $cm^2$ of neutrons of incident energy greater than 1.0 MeV) on the beltline region of the vessel. These calculations consider the vessel welds in the beltline region, which are identified as the weakest locations with respect to the risk of fracture. Often, however, the weld metal contains levels of impurities (e.g., Ni, Cu, P) which are known to exacerbate the effects of radiation-induced shifts in $RT_{NDT}$. For example, copper is often found in weld metal at concentrations of several tenths of one percent by weight, as a result of the copper coating formerly employed to prevent rusting of the wires of weld metal prior to use. The presence of such elements, at levels as low as tenths of one percent in the weld metal content, can severely affect the value of $\Delta RT_{NDT}$, and thus lead to severe restrictions in plant operation, up to and including cessation of plant operation.

Regulations enforced by agencies such as the U.S. Nuclear Regulatory Commission generally require that plant-specific evaluations consider conservative interpretations of available data on the actual weld metal used in a particular reactor vessel. These data might involve limited archive samples of the plant's weld metal that were saved at the time of fabrication, or might consider data for other vessels fabricated at roughly the same time or under similar conditions or with a similar batch of materials. However, these samples are relatively small in number. Since the impurity characteristics of the weld metal can exhibit significant wire-to-wire variations, this process can lead to significant inaccuracy in characterizing a reactor.

Background information relating to PGNAA can be found in U.S. Pat. No. 5,539,788, filed Jul. 23, 1996, "Prompt Gamma Neutron Activation Analysis System," which is hereby incorporated by reference. The experimental and analytical data presented therein demonstrate that the disclosed methods and system are capable of measuring trace element concentrations within a material sample by achieving extremely high signal-to-noise ratios. This technology is adapted in accordance with the present invention for use in detecting embrittlement-enhancing elements in the weld joints of an RPV. Background information relating to both the structure of an RPV and the inspection of an RPV for cracks, by way of visual or ultrasonic means, is disclosed in U.S. Pat. No. 4,728,482, Mar. 1, 1988, "Method for Internal Inspection of a Pressurized Water Nuclear Reactor Pressure Vessel."

SUMMARY OF THE INVENTION

A goal of the present invention is to provide a method and apparatus for evaluating the local content of elemental impurities at multiple locations of the reactor vessel weld metal. The invention is to be utilized to obtain a better understanding of the fracture risk associated with a specific plant, thus leading to significant savings to utility customers through reduced servicing and greater plant up-time. In addition, the invention will permit regulatory operating restrictions on nuclear power generation systems to be reduced considerably as a result of the knowledge gained of the spatial profile of embrittlement-enhancing elements within the weld structure of the reactor pressure vessel.

According to a presently preferred embodiment of the invention, a method for analyzing a weld of an RPV includes the steps of irradiating the weld with a neutron burst to effect an emission of gamma radiation from the weld; acquiring gamma radiation data indicative of the number or intensity of gamma rays and energies of the gamma rays during a predetermined time interval; and analyzing the gamma data to detect the presence and determine the amount of a prescribed constituent element in the weld. Preferably, groups of gamma radiation data are acquired during a plurality of time intervals, with each group being indicative of the number or intensity of gamma rays and energies of the gamma rays during a corresponding time interval. Moreover, the analyzing step preferably comprises determining the amount of the prescribed constituent element to an accuracy of about 0.1% by weight of the irradiated portion of the weld.

Other features of the present invention are disclosed below.

BRIEF DESCRIPTION OF THE DRAWINGS

FIG. 1 depicts a fragmentary, cross-sectional view of a system for performing in situ inspection of reactor vessel weld metal in accordance with the present invention.

FIG. 2 schematically depicts another embodiment of an RPV inspection system in accordance with the present invention.

DETAILED DESCRIPTION OF PREFERRED EMBODIMENTS

The present invention employs PGNAA to detect small amounts of embrittlement-enhancing elements. As disclosed in U.S. Pat. No. 5,539,788, PGNAA provides the capability for in situ measurement of concentrations of contaminant elements in materials at levels as low as tens of ppm for elements such as mercury or cadmium, within minutes to hours. For metals such as nickel or copper, measurements taking, e.g., one to several hours are expected to quantify concentrations in the tenths of percent range of concern in RPV fracture risk determination.

The PGNAA Method

In a PGNAA process, energetic neutrons from a source impinge on the sample to be interrogated, and the neutrons propagate through the material while undergoing various nuclear reactions. As a result of these reactions, the energy of the neutrons is reduced, ultimately to a value which is comparable to the thermal energy of the surrounding atoms. At this point, the neutrons are described as "thermal" neutrons; the slowing down process is termed "moderation" or "thermalization. " As discussed below, it is at this point that the neutron generally experiences the highest probability of interaction with the nuclei, in the form of "radiative capture"—i.e., the capture of the thermal neutron by a nucleus, with the attendant emission of one or more gamma rays.

Immediately following a nuclear reaction between one of the neutrons and the nucleus of one of the atoms of a constituent element of the sample, the resulting residual nucleus is left in an excited state, from which it promptly returns to its ground state—i.e., within $10^{-14}$ seconds. This return to the ground state is accompanied by the emission of one or more "prompt" gamma rays. The energy of each emitted prompt gamma ray results from the quantum structure of the emitting nucleus, and therefore determines the elemental identity of that nucleus. From a knowledge of the nuclear reaction which has occurred, the identity of the original nucleus (and therefore the original constituent element) is determined. The detected prompt gamma ray is therefore a signature of the original constituent element. After irradiation of the medium with a known number of neutrons, the yield of the appropriate "signature" gamma rays is a measure of the concentration of the element of concern within the sample.

As a result of the neutron irradiation of the material being interrogated, nuclear reactions occur between the neutrons and all the elements present in the sample, at rates determined by the atomic concentrations and inherent reaction probabilities (cross sections) characterizing the individual elements. By detecting the emitted gamma rays and displaying their yield as a function of gamma energy, the yields of selected signature gamma rays provide a measure of the concentrations of elements of concern within the interrogated sample. Moreover, the concentrations of multiple elements of concern can be measured in a single neutron irradiation.

High-Sensitivity PGNAA

Nuclear reactions, including neutron-induced reactions, proceed on a time scale in the range of $10^{-18}$ to $10^{-14}$ seconds, which is essentially instantaneous for electronic timing purposes. However, moderation of energetic (~MeV) neutrons to thermal energies requires times of the order of microseconds. Once produced, approximately one-half of the thermal neutrons will undergo nuclear reactions approximately every 200 to 300 microseconds. Therefore, the time scale of radiative capture—(n.γ)reactions—is of the order of hundreds of microseconds.

Neutron-induced reactions such as (n,n'), (n,2n), and most (n,p) reactions are produced only with fast neutrons (i.e., with energies in the range of keV to MeV or higher). Since no thermalization is required, these reactions occur essentially instantaneously, or at the same time that a source of fast neutrons is present. Therefore, if a pulsed electronic source is used and data are collected on a time structure on the hundreds of microseconds scale, a time separation of thermal and fast neutron-induced gamma rays can be achieved.

Previous PGNAA work had been limited by lack of sensitivity. For work employing pulsed neutron generators, the short pulse durations (1–5 microseconds) were characterized by extremely high instantaneous neutron emission rates, and the resulting gamma ray flux was so large that the detector electronics were paralyzed. In addition, all systems—whether using electronic or isotopic neutron sources—were hampered by relatively poor signal-to-background ratios for peaks from trace constituents in a sample. In the system disclosed in U.S. Pat. No. 5,539,788, the detection of gamma rays of interest is facilitated by exploiting the time sequence of neutron-induced reactions discussed above. This process is described in detail in U.S. Pat. No. 5,539,788, and one can observe that gamma rays produced by fast neutron-induced reactions are collected separately from most of the gamma rays produced by thermal neutron-induced processes. One can also observe that, since the gamma rays from thermal neutron-induced nuclear reactions are collected over only a limited duty cycle (generally 10 to 20 percent), these gamma ray spectra bear only a corresponding fraction of background from ubiquitous sources such as long-lived isotopes in the natural environment or short-lived isotopes produced by the neutron irradiation. Hence, the timing approach described in U.S. Pat. No. 5,539,788 achieves high signal-to-background ratios.

It should also be noted that the above-described method avoids the intense gamma ray background produced by many isotopic neutron sources, such as $^{252}$Cf, since electronic neutron generators produce virtually no associated gamma ray field. In the RPV inspection application of the present invention, where gamma ray background from long term vessel activation is already an issue, it is advantageous to avoid the additional burden of a high gamma ray background from the source.

An additional consideration in high-sensitivity PGNAA is the finite count rate throughput of the gamma ray detector and associated electronics. At the present time, the maximum achievable gamma ray pulse throughput is about 100,000 counts per second with a system dead time due to pulse pileup of 60 to 90 percent, depending on spectrum characteristics. In practice, the high gamma ray energies encountered in PGNAA limit the count rate throughput to 20,000 to 30,000 counts per second. In applications where fast neutron-induced gamma rays are of primary interest, the system can be operated at lower source intensity to optimize the system throughput for data from gamma rays produced during the neutron pulses. The pulsing scheme can also be adjusted so that only a minimum of neutron thermalization occurs before collection of gamma ray data.

The presently preferred embodiment of the PGNAA system utilizes the following equipment to produce high signal-to-background acquisition of high count rate gamma ray spectral data:

Large-volume, neutron-resistant, high resolution gamma ray detector;

High-throughput pulse processing electronics:
  high speed transistor reset preamplifier;
  state-of-the-art spectroscopy amplifier;
  450 MHz Wilkinson analog-to-digital converter;

Large-volume, high count rate, anti-Compton suppression shield (to be replaced in the reactor vessel weld inspection application with a high-density radiation shielding);

Unique, customized pulsed neutron generator; Acquisition Interface Module, governing the correlation of neutron pulsing and gamma ray data acquisition;

Computer control system utilizing commercially available technology for:
  system control with nanosecond timing capabilities;
  time-sequenced multi-channel analysis for gamma ray spectroscopy;
  spectroscopy software, including peak search, area integration, area uncertainty evaluation, and nuclear data library match capabilities.

The Vessel Weld Inspection Application

According to the present invention, high sensitivity PGNAA is applied to the in situ inspection of RPV weld metal to determine the spatial profile (as a function of vessel height and azimuthal location) of the concentration of nickel, copper or other elements of concern (e.g., phosphorus). As described above, this information can have a significant impact on regulatory restrictions placed on reactor operation, as well as on regulatory requirements for pressure vessel annealing.

In the following discussion, the physical and radiation environments affecting the vessel inspection application are described. Technical issues are addressed, including the interrogation depth achievable with this method, potential interfering signals from the weld metal or base metal of the reactor vessel, potential interference to the nickel measurement from the abundance of nickel in the stainless steel cladding attached to the reactor vessel inner radius, and the effects of the ambient radiation field on the detection electronics.

Physical Environment

FIG. 1 schematically depicts a system in accordance with the present invention. In this exemplary implementation of the invention, a carbon steel pressure vessel 10 has a horizontal weld joint 12 to be inspected. Stainless steel cladding 14 covers the weld 12. A concrete wall 16 defines a pressure vessel cavity 18 in which water may be permitted to flow. A gamma detector 20, surrounded by heavy metal shields 20a and 20b, and a sheet 22 of neutron absorbing material, e.g., cadmium, are positioned adjacent the weld region 12, and an Acquisition Interface Module (AIM) and associated computer, collectively designated with reference numeral 24, and a neutron source 26 are employed to measure the amount of the target embrittlement-enhancing elements present in the weld. A housing 28 encloses the detector 20, sheet 22, and neutron source 26. The housing can be employed to support a combination of moderating, reflecting and absorbing materials 32, as appropriate. Typically, the RPV is 6 to 9 inches (15.2–22.9 cm) thick, with the stainless steel cladding 14 welded to the inner radius of the vessel 10.

FIG. 2 depicts a top view of an implementation in which a vertical weld joint 12' is inspected. In this example, a collimator containing a narrow aperture, 30 is employed to reduce the effects of background radiation on the measurement. Thus, in preferred embodiments of the present invention, interference is avoided by making the detector 20 both narrowly collimated and shielded by several inches of heavy metal.

In the weld inspection application, the inspection process is nominally expected to be conducted during time periods (e.g., In-Service Inspections, or ISI, required by Section X of the ASME Boiler and Pressure Vessel Code) during which the core, core baffle and core barrel (i.e., lower internals, not shown in the drawings) have been removed from the vessel. To support radiation protection measures undertaken during ISI, the RPV will have been filled with water.

In the irradiation of the vessel wall from the water region, the thermalization of the incident neutrons results from three effects:

1) thermalization of neutrons in the water region preceding entry into the metal;

2) pre-thermalization in the water, followed by a final energy loss occurring in the vessel wall (or weld) steel; and 3) pre-thermalization of the neutrons in the water and steel, followed by thermalizing backscattering off the concrete (the intervening air provides negligible modification of the neutron number or energy distribution).

Measurements conducted at Westinghouse Electric Corporation (the assignee of the present invention) indicate that there is a significant thermal and epithermal flux at depths of up to approximately four inches (about 10 cm) into the steel, beyond the metal-water interface.

Signature Gamma Ray Energies and Depth of Interrogation

Table 1, below, lists the energies and yields of the main prompt gamma rays emitted as a result of thermal neutron radiative capture in nickel and copper. As the table indicates, both of these elements emit gamma rays with significant yields at energies both below 1000 keV and above 6500 keV. Only those gamma rays with energies greater than 6500 keV will contribute usefully to the measurement of copper and nickel in the vessel weld metal, since the gamma rays with energies less than 1000 keV will be heavily absorbed by the radiation shielding 20a, 20b (FIG. 1) designed to protect the detector from the background $^{60}$Co gamma rays.

TABLE 1

Principal prompt gamma rays emitted from nickel and copper

| NICKEL | | COPPER | |
|---|---|---|---|
| Gamma Ray Energy (keV) | Branching Ratio (γ's per 100 neutron captures) | Gamma Ray Energy (keV) | Branching Ratio (γ's per 100 neutron captures) |
| 283.1 | 3.34 | 203.1 | 7.21 |
| 339.5 | 2.78 | 278.3 | 32.69 |
| 465.1 | 12.98 | 343.9 | 5.46 |
| 877.9 | 3.86 | 385.2 | 7.58 |
| 6837 | 10.79 | 466.2 | 5.97 |
| 7537 | 4.47 | 579.8 | 2.91 |
| 7818.9 | 8.19 | 608.9 | 8.62 |
| 8533.4 | 16.98 | 648.4 | 2.6 |
| 8998.8 | 37.74 | 7306.2 | 8.09 |
| | | 7636.6 | 15.71 |
| | | 7914.5 | 30.82 |

As a reference, the thickness of iron required to attenuate a beam of gamma rays of energy 6800 keV down to 25 percent of its initial intensity is 2.3 inches (5.8 cm). The expected depth of interrogation for measurement of the concentration of copper or nickel in the vessel weld metal 12, 12' is roughly 2 to 2.5 inches (5–6.4 cm).

Interference from Iron

Of the gamma ray energies listed in Table 1, comparison has been made with the prompt gamma ray yield from the iron, the main constituent of the weld or base metals. This comparison indicates that the 7636.6 keV gamma ray emitted by copper experiences unacceptable interference from the 7631.1 keV gamma ray emitted by iron. Therefore, the 7636.6 keV gamma ray emitted by copper would not be employed in the vessel inspection application, based on the degree of energy resolution currently available in gamma ray detectors. However, the other nickel and copper prompt gamma rays of energy above 6500 keV do not experience such interference from iron.

Suppression of Cladding Interference

The nickel content of the stainless steel cladding 14 is typically five to ten percent. Because of the favorable geometry this region experiences relative to the gamma ray detector, the nickel prompt gamma rays emitted from this region would provide a signal that overwhelms that from the one percent or so of nickel in the weld metal beneath the clad. However, neutron dosimetry measurements have demonstrated that a narrow and thin (33 mil, or 0.8 mm) sheet 22, 22' of elemental cadmium (or another strong neutron absorber) placed over the clad in the region viewed by the gamma ray detector serves effectively to suppress the thermal neutron flux at the surface, while leaving unaffected the thermal flux beyond a 0.5-inch depth (i.e., in the clad region) in the steel. This "thermal flux depression" phenomenon is well understood, and the depth through which the thermal flux is suppressed can be increased by using a wider cadmium sheet. The depth of flux depression can in general be controlled by appropriate tailoring of the neutron spectrum outside the metal surface. Such tailoring can be accomplished in practice by combining predesigned layers of selected materials (designated by ref. no. 32 in the drawings) to cause more or fewer of the neutrons to enter the cadmium surface at thermal energy. In this way, the prompt gamma signal from the varying thicknesses of cladding 14 used in different reactor vessels (these typically range from 5/32 inch to 3/4 inch (0.4–1.9 cm)) can be effectively suppressed, allowing measurement of the nickel concentration in the vessel weld metal 12, 12' without interference.

Radiation Environment

Radiation dosimetry data from operating plants under ISI conditions (i.e., lower internals removed, reactor vessel flooded with water) indicate that the radiation environment in the water adjacent the vessel inner radius consists of approximately 100 R/hr of gamma ray radiation, comprised primarily of the gamma ray energies 1.1732 and 1.3325 MeV (the two gamma ray cascade emitted in the beta decay of $^{60}Co$). The primary source of this radiation is from activation of the cobalt content of the stainless steel clad 14.

Evaluation of the count rates resulting from the $^{60}Co$ gamma rays indicates that PGNAA measurements can be made in the presence of the cobalt gamma ray background provided a high-efficiency HPGe gamma ray detector, narrowly collimated and shielded by several inches of heavy metal, is utilized in the inspection system.

Sensitivity for Copper and Nickel

Laboratory tests (conducted without an external radiation field) have been conducted to demonstrate the feasibility of the above-described PGNAA method for vessel weld inspection. The following results have been reported:

- detection of copper at concentration levels ranging from one to four percent (by weight) in steel in less than one hour;
- detection of subsurface copper in steel uniformly distributed between 0.25-inch and 1-inch depths (0.6–2.54 cm);
- measurements indicating that the sensitivity of PGNAA for nickel is better than its sensitivity for copper; and
- demonstration of the method employing cadmium at the surface to selectively suppress the thermal neutron flux in the clad region. Projections made from the experimental data indicate that the sensitivity of an optimized PGNAA weld inspection system will satisfy the detection levels for copper and nickel required in this application.

The present invention is not limited to the presently preferred embodiments of the methods and apparatus described above. For example, the construction and arrangement of the gamma detector and its associated shielding, the cadmium neutron absorber, and the acquisition electronics may be modified within the teachings of the invention as needed for a particular RPV environment, as will be recognized by those skilled in the art. Accordingly, except where they are expressly so limited, the scope of protection of the following claims is not limited to the details specified above.

We claim:

1. A method for analyzing a weld of a reactor pressure vessel (RPV), comprising the steps of:

(a) irradiating said weld with a neutron burst from a neutron source, said burst characterized by an intensity and pulse width and duty cycle, and thereby effecting an emission of fast and thermal neutron-induced gamma radiation from said weld;

(b) acquiring gamma radiation data indicative of the number or intensity of gamma rays and energies of said gamma rays during a predetermined time interval, said acquiring step including a separate identification of fast neutron-induced and thermal neutron-induced gamma rays, and wherein said gamma radiation is collected over only a fraction of said duty cycle; and (c) analyzing said gamma data to detect the presence and determine the amount of a prescribed constituent element in said weld.

2. A method for analyzing a weld of a reactor pressure vessel as recited in claim 1, wherein step (b) comprises acquiring groups of gamma radiation data during a plurality of time intervals, each group being indicative of the number or intensity of gamma rays and energies of said gamma rays during a corresponding time interval.

3. A method for analyzing a weld of a reactor pressure vessel as recited in claim 1, wherein step (c) comprises determining the amount of said prescribed constituent element to an accuracy of about 0.1% by weight of the irradiated portion of the weld.

4. A method for analyzing a weld of a reactor pressure vessel as recited in claim 1, wherein said RPV comprises a metal cladding covering the irradiated surface.

5. A method for analyzing a weld of a reactor pressure vessel as recited in claim 4, wherein said metal cladding comprises cobalt.

6. A method for analyzing a weld of a reactor pressure vessel as recited in claim 1, wherein the method is performed in an environment containing a gamma radiation field of about 100 R/hr.

7. A method for analyzing a weld of a reactor pressure vessel as recited in claim 6, wherein step (a) is carried out with a neutron source submerged in water.

8. A method for analyzing a weld of a reactor pressure vessel as recited in claim 1, wherein an element selected from the group consisting of copper, nickel and phosphorous is measured.

9. A method for analyzing a weld of a reactor pressure vessel as recited in claim 1, wherein the RPV is an off-line, previously irradiated, water-containing RPV having an internal metal cladding covering the weld, characterized by the steps of:
   (1) opening the off-line RPV; and then
   (2) introducing a neutron source into water in the off-line RPV before irradiating the vessel with the neutron source.

10. A method for analyzing a weld of a reactor pressure vessel as recited in claim 9, wherein the cladding contains at least about 8% by weight nickel.

11. A method for analyzing a weld of a reactor pressure vessel as recited in claim 10, wherein the weld contains less than 1% by weight nickel and the amount of nickel is to be determined.

12. A method for analyzing a metal body having a surface, comprising the steps of:
   (a) irradiating said surface with a neutron burst from a neutron source, said burst characterized by a duty cycle, and thereby effecting an emission of gamma radiation from said surface;
   (b) acquiring gamma radiation data indicative of the number or intensity of gamma rays and energies of said gamma rays during a predetermined time interval, said acquiring step including a separate identification of fast neutron-induced and thermal neutron-induced gamma rays, and wherein said gamma radiation is collected over only a fraction of said duty cycle; and
   (c) analyzing said gamma data to detect the presence and determine the amount of prescribed constituents of said metal body.

13. A method as recited in claim 12, wherein step (b) comprises acquiring groups of gamma radiation data during a plurality of time intervals, each group being indicative of the number or intensity of gamma rays and energies of said gamma rays during a corresponding time interval.

14. A method as recited in claim 12, wherein step (c) comprises determining the amount of said constituents to an accuracy of about 0.1% by weight of the irradiated portion of the metal body.

15. A method as recited in claim 12, wherein said metal body comprises a metal cladding covering the irradiated surface.

16. A method as recited in claim 15, wherein said metal cladding comprises cobalt.

17. A method as recited in claim 12, wherein the environment surrounding the neutron source contains a gamma radiation field of at about 100 R/hr.

18. A method as recited in claim 12, wherein said neutron source is submerged in water while it is irradiating the metal body.

19. A method as recited in claim 12, wherein an element selected from the group consisting of copper, nickel and phosphorous is measured.

20. A method as recited in claim 12, wherein the metal body is formed of sections welded together and constituents of the weld are determined.

21. A method as recited in claim 20, wherein the metal body is a reactor pressure vessel (RPV).

22. A method as recited in claim 21, wherein the RPV is an off-line, previously irradiated, water-containing RPV having an internal, cobalt-containing, metal cladding covering the weld, characterized by the steps of:
   (1) opening the off-line RPV; and then
   (2) introducing a neutron source into water in the off-line RPV before irradiating the vessel with the neutron source.

23. A method as recited in claim 22, wherein the constituents of a weld between adjacent sections of the RPV under the cladding are determined.

24. A method as recited in claim 23, wherein a constituent selected from the group consisting of copper, nickel and phosphorous is determined.

25. A method as recited in claim 24, wherein the cladding contains at least about 8% by weight nickel.

26. A method as recited in claim 25, wherein the weld contains less than 1% by weight nickel and the amount of nickel is to be determined.

* * * * *